(12) United States Patent
Karpiel

(10) Patent No.: US 8,277,392 B2
(45) Date of Patent: *Oct. 2, 2012

(54) BIOPSY COLLECTION DEVICE

(75) Inventor: John A. Karpiel, Winston-Salem, NC (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/004,123

(22) Filed: Jan. 11, 2011

(65) Prior Publication Data

US 2011/0105950 A1    May 5, 2011

Related U.S. Application Data

(63) Continuation of application No. 11/877,135, filed on Oct. 23, 2007, now Pat. No. 7,878,983.

(60) Provisional application No. 60/854,537, filed on Oct. 26, 2006.

(51) Int. Cl.
*A61B 10/00* (2006.01)
*A61B 1/00* (2006.01)

(52) U.S. Cl. ........................................ 600/564; 600/104

(58) Field of Classification Search .......... 600/562–567, 600/104, 105, 115, 116; 606/45–47, 127, 606/170
See application file for complete search history.

(56) References Cited

U.S. PATENT DOCUMENTS

| 6,273,860 | B1 | 8/2001 | Kostylev et al. |
| 7,878,983 | B2 * | 2/2011 | Karpiel ......................... 600/564 |
| 2005/0222519 | A1 | 10/2005 | Simpson |
| 2005/0261674 | A1 | 11/2005 | Nobis et al. |
| 2006/0116603 | A1 | 6/2006 | Shibazaki et al. |

FOREIGN PATENT DOCUMENTS

| EP | 1 834 599 A | 9/2007 |
| EP | 1 870 015 A1 | 12/2007 |
| WO | WO 2006/064868 A1 | 6/2006 |

OTHER PUBLICATIONS

International Search Report mailed Mar. 25, 2008 for International Application No. PCT/US2007/082188.

* cited by examiner

*Primary Examiner* — Brian Szmal
(74) *Attorney, Agent, or Firm* — Brinks Hofer Gilson & Lione

(57) ABSTRACT

A method and device for removing tissue from a patient during a biopsy procedure utilizing a biopsy collection device are provided. The biopsy collection device includes a body portion configured for attachment to an endoscope and a receptacle portion configured to retain a portion of tissue removed from a target site during the biopsy procedure. The biopsy collection device further includes a passageway configured to receive a biopsy sampling device, such as a pair of forceps, passing through the endoscope to the target site.

20 Claims, 12 Drawing Sheets

BIOPSY COLLECTION DEVICE

RELATED APPLICATIONS

This application is a continuation of U.S. application Ser. No. 11/877,135, filed Oct. 23, 2007, which claims the benefit of U.S. Provisional Application No. 60/854,537, filed Oct. 26, 2006, which are incorporated by reference herein in their entirety.

TECHNICAL FIELD

The invention generally relates to a medical device for removal and collection of portions of the mucuosa and/or submucosa tissue during medical procedures.

BACKGROUND

Diagnostic and therapeutic gastrointestinal endoscopy procedures are commonly used to gain access to the digestive tract for the purpose of removing tissue during biopsy procedures. Common endoscopy procedures include incision and ablation through various known mechanisms.

Techniques for obtaining tissues during biopsy procedures and/or other medical procedures involving tissue removal can be difficult. For example, regular endoscopic surveillance procedures involving multiple biopsies are advocated to detect development of dysplasia as a precancerous lesion. These procedures, which include endoscopic mucosal resection (EMR), involve the removal of a fragment (i.e., resection) of the digestive wall including the mucosal membrane. This procedure typically removes a part or even all of the submucosa. Endoscopic mucosectomy is a curative endoscopic procedure which is intended for sessile benign tumors and intramucosal cancers. The procedure makes it possible to determine precisely the nature of subsequent treatment required.

The incision devices currently utilized in biopsy procedures often make tissue removal difficult. These problems are compounded by the thick gastrointestinal wall that the incisions are performed within. Considerable time and effort is therefore required by the physician to incise and remove the desired tissue. The inability to quickly remove tissue increases patient trauma. Moreover, current incision devices cannot remove unfragmented portions of tissue. Assessment of fragmented tissue becomes increasingly difficult during sampling as compared to assessment of unfragmented tissue. Furthermore, fragmented resection of early cancers may lead to a higher rate of local tumor recurrence.

Some biopsy procedures are cumbersome and time consuming due to problems incising a tissue sample from a target site because often a separate procedure needs to be performed to incise and collect a biopsy of the target site. For example, a biopsy of the target site is typically obtained by passing a different instrument to the target site and then cutting away and removing the tissue sample. The introduction of separate devices to the patient for treating the tissue increases the procedure time and causes patient discomfort.

In view of the drawbacks of current medical devices, there is a need for a medical device that can more efficiently remove tissue and debris during biopsy procedures without the need of multiple exchanges of medical devices while significantly reducing the duration of the biopsy procedure.

SUMMARY

Accordingly, a biopsy collection device is provided that resolves or improves upon one or more of the above-described drawbacks.

In one aspect of the present invention, a biopsy collection device is provided. The biopsy collection device includes a body portion having a proximal end portion and a distal end portion, the proximal end portion is configured for attachment to an endoscope. The biopsy collection device further includes a passageway extending through the body portion where the passageway is configured to receive a biopsy sampling device extending from the endoscope and passing through the passageway to a target site. The biopsy collection device includes a receptacle portion operably connected to the passageway and configured to retain a sample removed from the target site during a biopsy procedure.

In another aspect of the present invention, a biopsy collection device is provided. The biopsy collection device includes a body portion having a proximal end portion, a distal end portion and a substantially hollow interior. The proximal end portion is configured for attachment to an endoscope. The biopsy collection device further includes a receptacle portion defined in the distal end portion and configured for retaining a sample. The receptacle portion includes a wall extending proximally from the distal end portion into the substantially hollow interior and an opening through the receptacle portion and defined by the wall. The biopsy collection device also includes a passageway extending between the proximal end portion and the opening, wherein the passageway is configured for receiving a biopsy sampling device passing from the proximal end portion through the passageway to a target site to obtain the sample.

In another aspect of the present invention, method for removing tissue during a biopsy procedure is provided. The method includes providing a biopsy collection device having a body portion configured for attachment to an endoscope and a receptacle portion configured to receive a portion of tissue removed from a target site. The method also includes advancing the endoscope towards the target site of the tissue to be removed, and loading a biopsy sampling device through the endoscope, wherein the sampling device is extended past a distal end of the biopsy collection device. The method further includes grasping tissue from the target site, retracting the biopsy sampling device into the biopsy collection device; and delivering tissue to a lumen in the receptacle portion and retaining the tissue therein.

BRIEF DESCRIPTION OF THE DRAWINGS

Embodiments will now be described by way of example with reference to the accompanying drawings, in which.

DETAILED DESCRIPTION OF THE PREFERRED EMBODIMENTS

Figure 1:
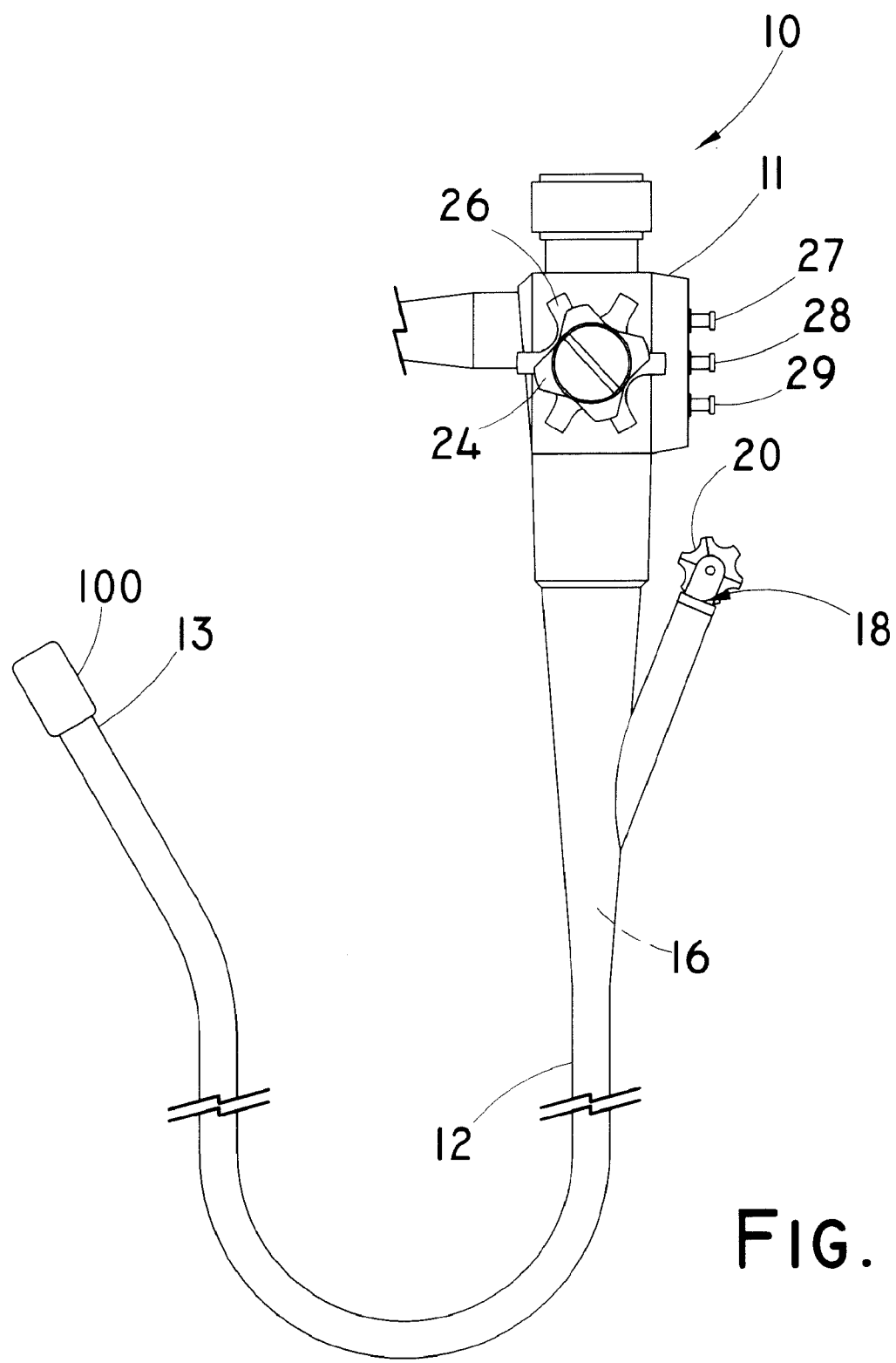
FIG. 1 is a perspective view of a biopsy collection device attached to an endoscope in accordance with an embodiment of the present invention.

The embodiments are described with reference to the drawings in which like elements are referred to by like numerals. The relationship and functioning of the various elements of the embodiments are better understood by the following detailed description. However, the embodiments as described below are by way of example only, and the invention is not limited to the embodiments illustrated in the drawings. It should also be understood that the drawings are not to scale and in certain instances details have been omitted, which are not necessary for an understanding of the embodiments, such as conventional details of fabrication and assembly.

FIGS. 2-7 illustrate an embodiment of the biopsy collection device 100 prior to attachment to the endoscope 10. The biopsy collection device 100 comprises a body portion 120 and a receptacle portion 130, wherein the receptacle portion 130 is configured to receive and store tissue and debris removed during a biopsy procedure.

FIG. 1 illustrates a biopsy collection device 100 for the removal and storage of tissue upon performing a biopsy in accordance with the present invention. The biopsy collection device 100 is shown attached to a distal end 13 of an endoscope 10. The endoscope 10 may be a conventional endoscope with an operating control portion 11 and a flexible insertion tube 12. The endoscope 10 further comprises a biopsy port 18 extending through an operating biopsy channel 16 of the present invention. The biopsy collection device 100 is compatible for use with the endoscope 10 during biopsy procedures, and can also be implemented in other medical procedures. For example, the biopsy collection device 100 may be implemented in procedures such as endoscopy, gastroscopy, sigmoidoscopy and colonoscopy, esophago gastro duodenoscopy (EGD), endoscopic retrograde cholagiopancreatography (ERCP), endoscopic mucosal resection (EMR), and bronchoscopy.

Figure 2:
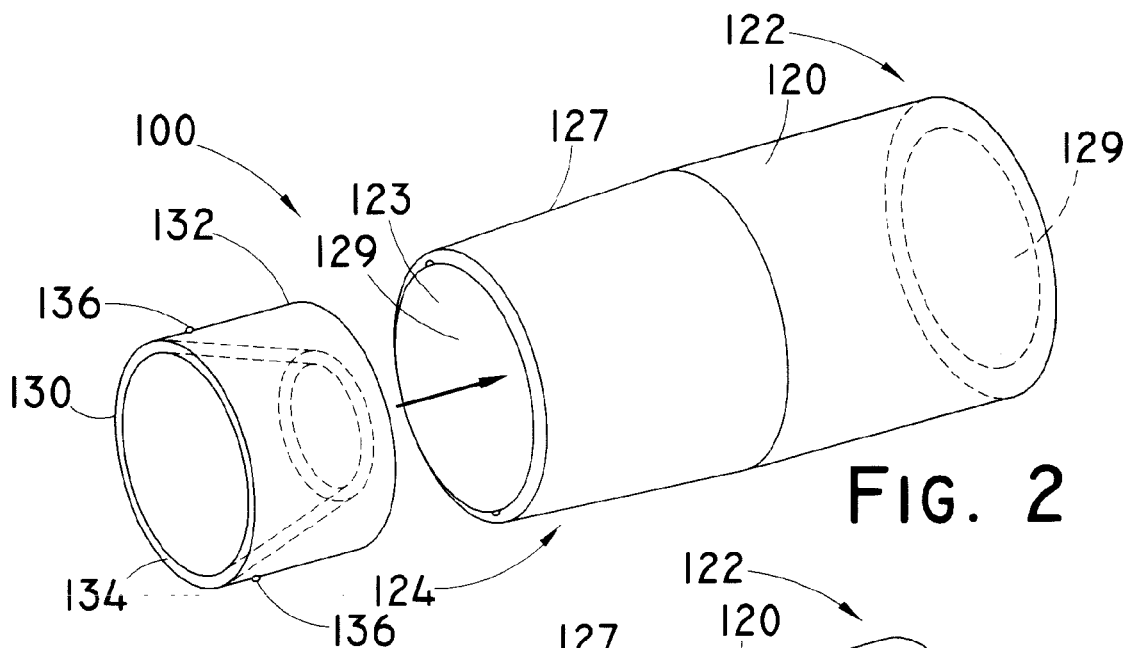
FIG. 2 is a perspective view of the biopsy collection device of FIG. 1.

As shown in FIG. 2, the biopsy collection device 100 may include a body portion 120 having a proximal end 122 and a distal end 124 and a receptacle portion 130 at the distal end 124. The device 100 further comprises a passageway 129 extending through the body portion 120 for receiving medical devices when the biopsy collection device 100 is coupled to the endoscope 10. The passageway 129 is configured to receive medical devices that are passed through an operating biopsy channel 16 in the endoscope 10 and through the body portion 120 to remove tissue from a target site of a patient. The passageway 129 forms a generally hollow interior of the body portion 120. As shown in FIG. 2, the receptacle portion 130 of the biopsy collection device 100 includes a proximal end 132 and a distal end 134, wherein the distal end 134 includes a lumen 131 to receive and store tissue or debris during the biopsy procedure. (See FIG. 13).

Figure 16:
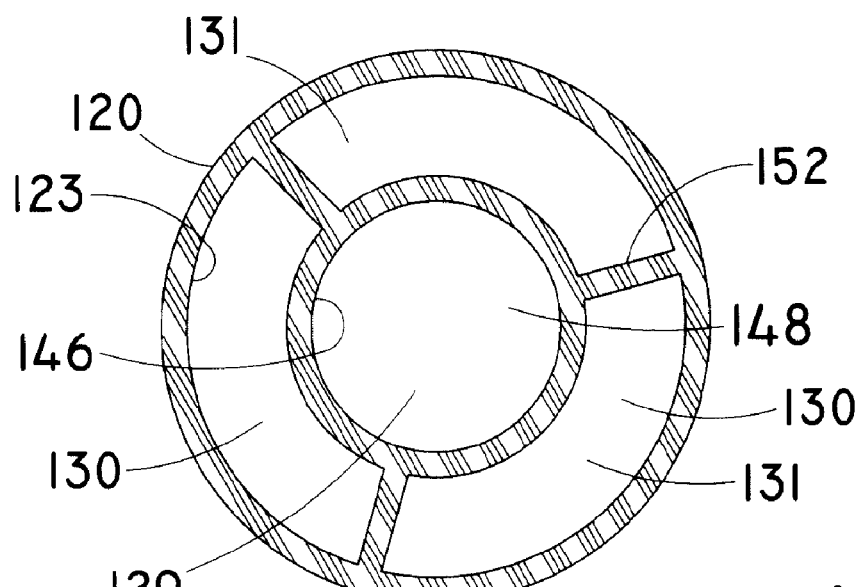
FIG. 16 is a cross-sectional view through the biopsy collection device showing a central passageway and first and second receptacle portions.
Figure 17:
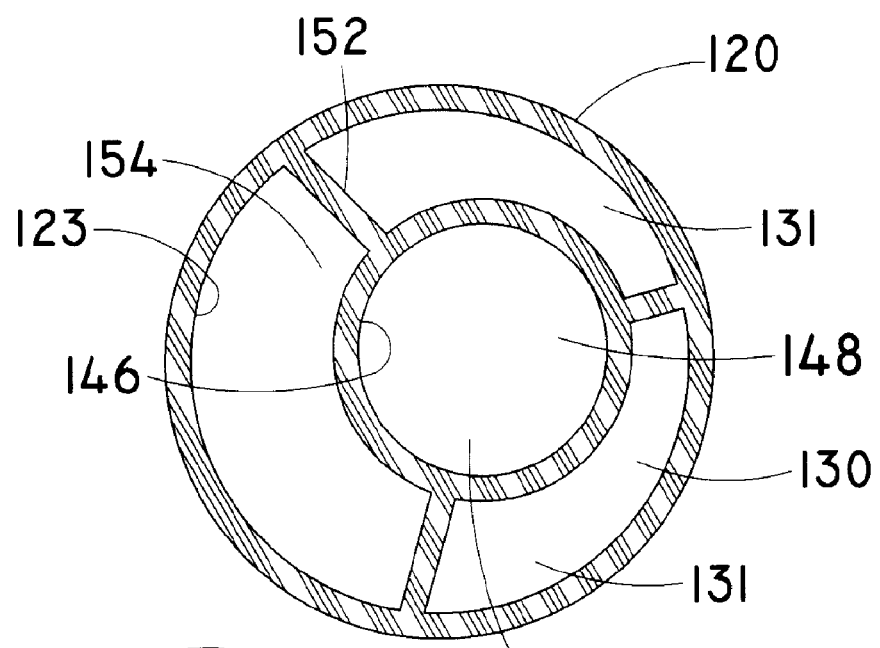
FIG. 17 is a cross-sectional view through the biopsy collection device showing an off-set passageway.

As shown in more detail in FIGS. 11-14, the biopsy collection device 100 includes the receptacle 130 at the distal end 124 of the body portion 120. The receptacle 130 includes at least one lumen 131 formed in the receptacle 130 between a wall 123 of the body portion 120 and a wall 146 of the receptacle portion 130. In some embodiments, the wall 146 is upstanding from the distal end 134 of the receptacle portion 130 and directed toward the proximal end 132. The wall 146 may further form a circumferential opening 148 defined in the receptacle portion and operably connected to the passageway 129. The opening 148 allows the medical device to extend to the exterior of the biopsy collection device 100 to the biopsy site. The opening 148 may be centrally positioned within the biopsy collection device 100 as shown in FIG. 16 or off-set as shown in FIGS. 15 and 17. The opening 148 may have a reduced diameter that permits the passage of a medical device therethrough, but inhibits passage of the sample through the opening 148 once the sample has been collected in the receptacle portion 130. In some embodiments, at least a portion of the wall 146 may be angled inward and away from the wall 123 from the distal end 134 to the proximal end 132. The angled wall 146 provides a larger lumen for ease of sample placement therein.

Figure 11:
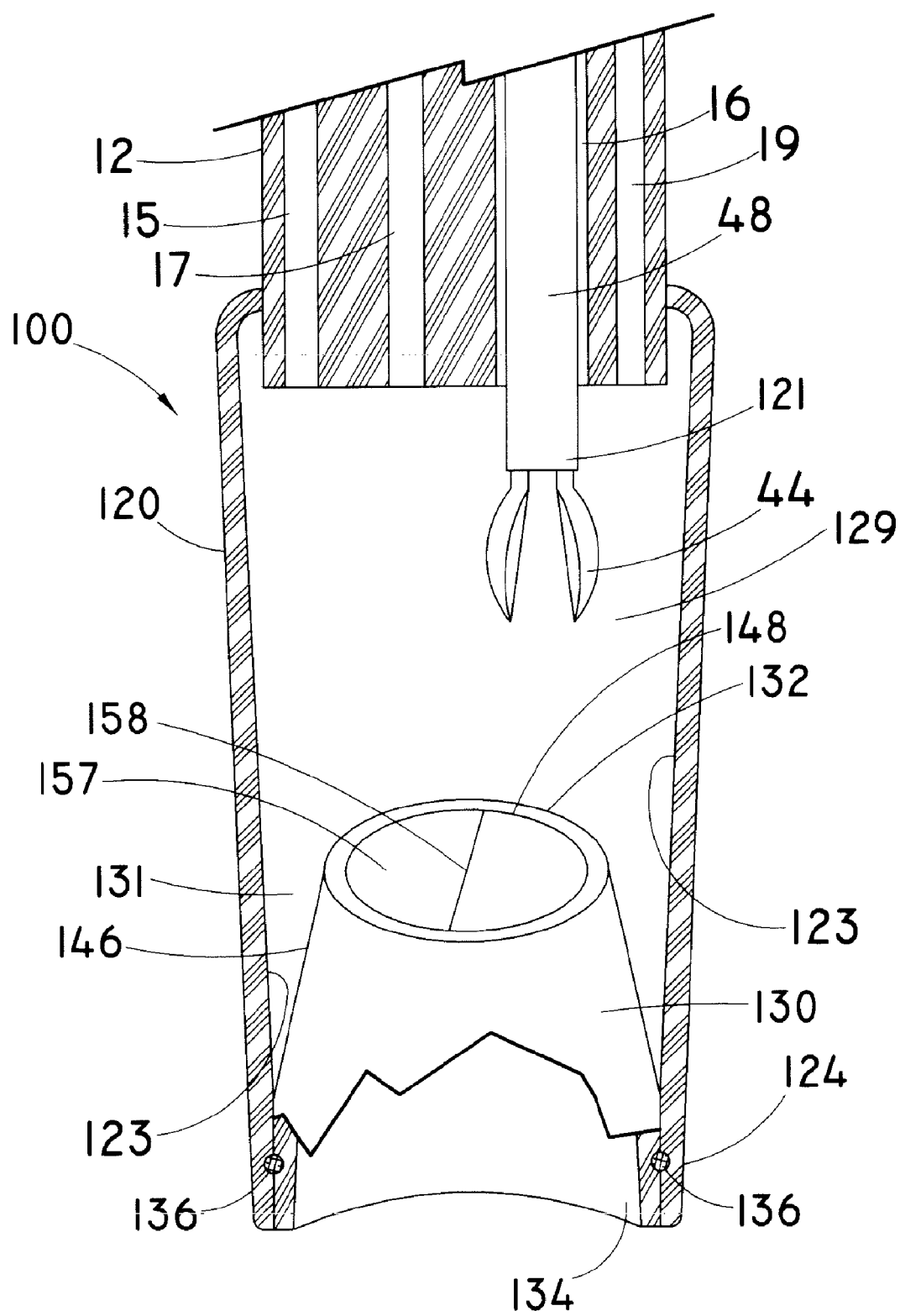
FIG. 11 is partial cross-sectional view of the biopsy collection device of FIG. 9, wherein the pair of forceps is inserted into the passageway of the body portion of the biopsy collection device.
Figure 14:
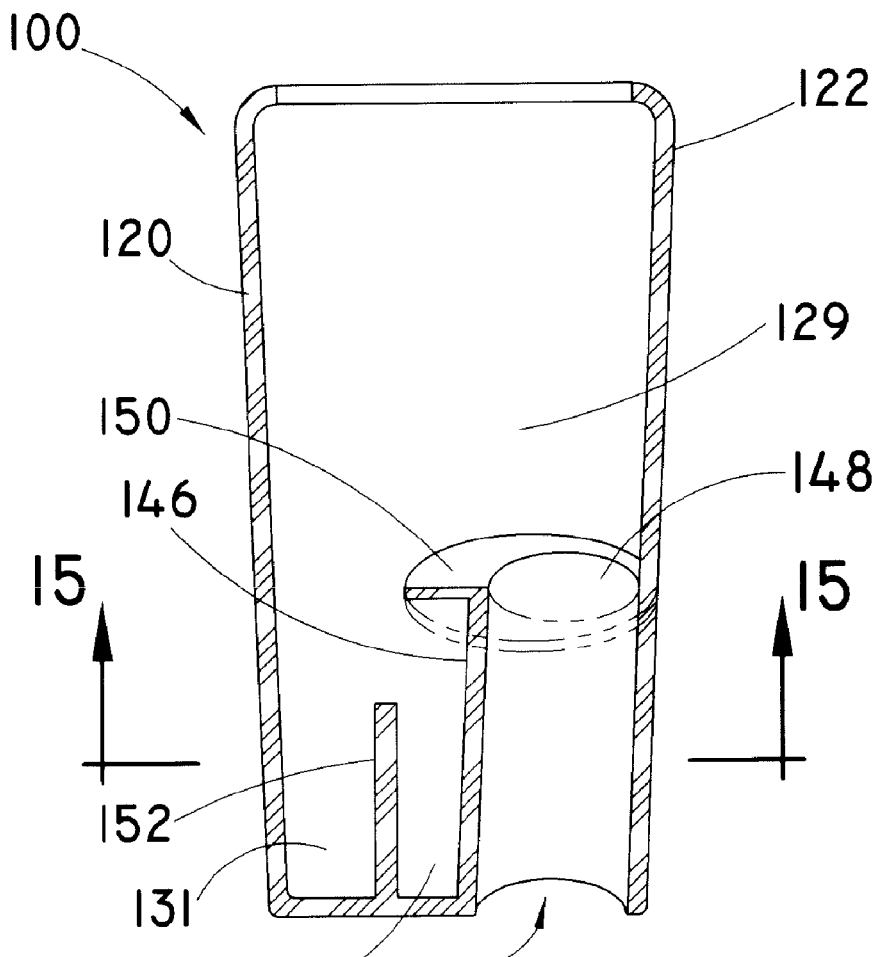
FIG. 14 is a partial cross-sectional view of a biopsy collection device having a first and second receptacle portion.
Figure 15:
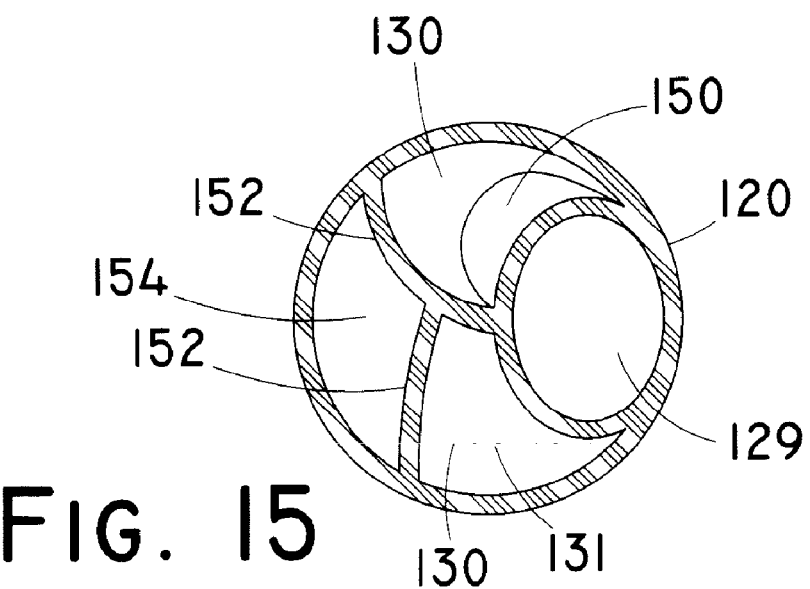
FIG. 15 is a cross-sectional view through the line B-B showing the passageway, the first and second receptacle portions.

As shown in FIGS. 14 and 15, the wall 146 may include a flange 150 extending partially over the lumen 131 to help retain the sample in the lumen 131. The flange 150 may be provided as a flexible rim extending over the lumen 131 around the opening 148 to retain the sample in the lumen 131. The flange 150 may be flexible enough to allow the sampling device to deposit the sample in the lumen 131, but rigid enough so that the sample is retaining in the lumen 131 for the remainder of the procedure. In some embodiments, the wall 146 may be flexible and/or tapered inward toward the opening 148 so that the forceps 44 may pass through the opening 148 but the flexible walls 146 inhibit the passage of the samples stored in the lumens 131 out of the biopsy collection device 100. As shown in FIG. 11, some embodiments may include a septum 157 covering the opening 148 to inhibit the passage of the samples back out of the opening 148. The septum 157 may include a slit 158 for passage of the medical device therethrough. The forceps 44 may also be used to compress the tissue to draw the sample into the receptacle 130 through the opening 148.

The lumen 131 may be sectioned into a plurality of lumens 131 by one or more wall partitions 152 upstanding from the distal end 134 of the receptacle portion 130. In some embodiments, the distal end of the receptacle portion 130 may include a viewing portion 154 that is optically configured for providing a viewing window for an optical device as shown in FIG. 15. In some embodiments, a portion of the biopsy collection device 100 is substantially transparent to facilitate viewing of the target area.

The biopsy collection device 100 may comprise a unitary structure (see FIG. 4) or multiple components (see FIGS. 2-3) being slidably connected or other suitable design variations and fall within the scope of the invention.

Figure 5:
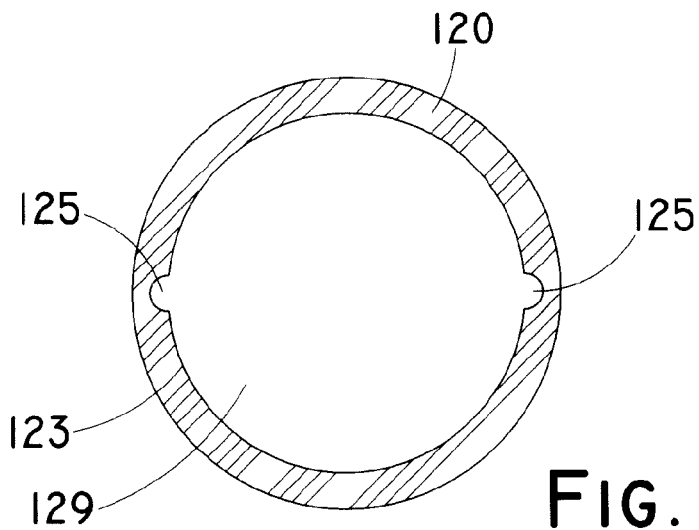
FIG. 5 is a cross-sectional view of the body portion of the biopsy collection device of FIG. 2.
Figure 6:
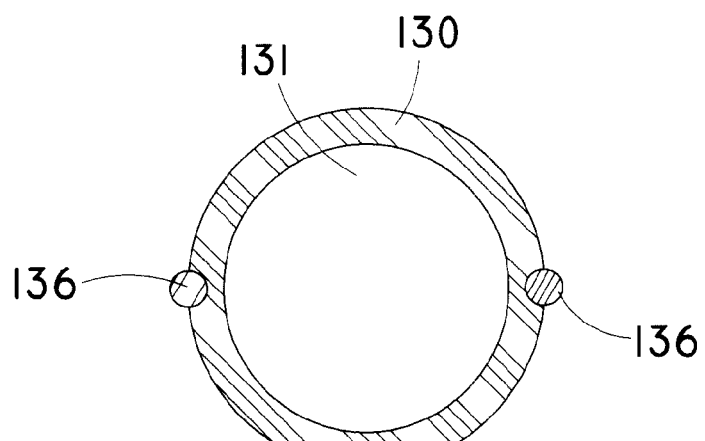
FIG. 6 is a top sectional view of the receptacle portion of the biopsy collection device of FIG. 2.
Figure 7:
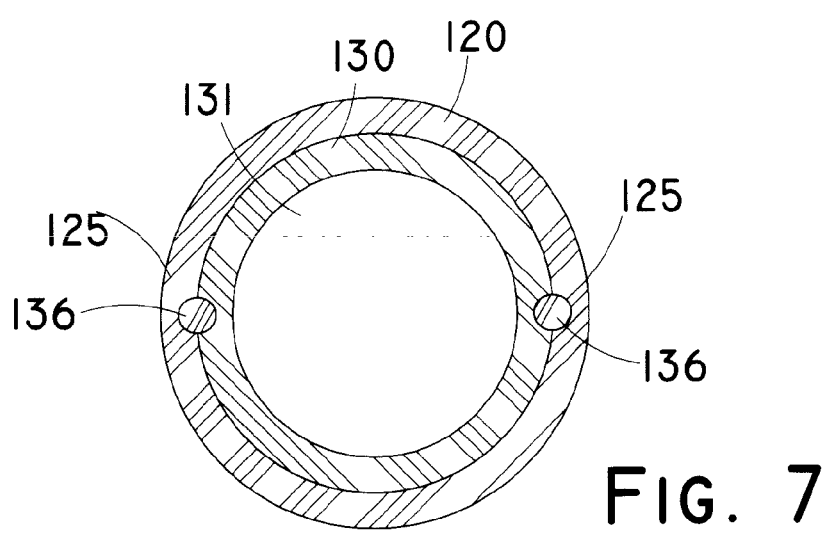
FIG. 7 is a partial cross-sectional view of the body portion and the receptacle portion of the biopsy collection device of FIG. 2.

The body portion 120 of the biopsy collection device 100 also includes an inner wall 123. The inner wall 123 may include grooves 125 located along the surface of the inner wall 123. As shown in FIG. 5-7, the grooves 125 provide an opening to receive protuberances 136 of the receptacle portion 130 when the biopsy collection device 100 is provided in a multi-component configuration. The grooves allow the receptacle portion 130 to be attached and detached from the body portion 120 of the device 10 to remove tissue and debris.

Figure 4:
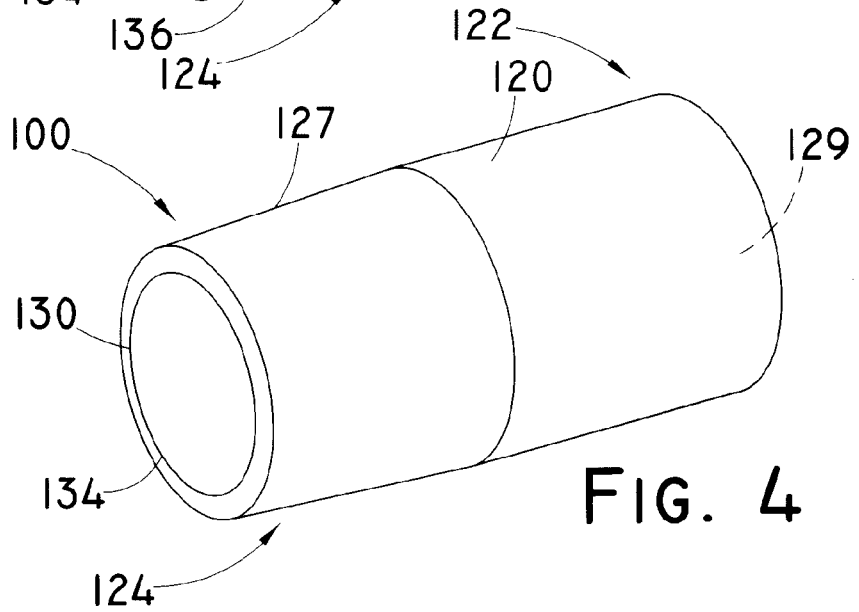
FIG. 4 is a perspective view of the body portion and the receptacle portion of the biopsy collection device showing a unitary configuration.

In the embodiment providing multiple portions, the receptacle portion 130 comprises two protuberances 136 for slidably connecting the receptacle portion 130 to the body portion 120. The receptacle portion 130 is configured to slidably move relative to the inner wall 123 of the body portion 120 and align the protuberances 136 with the grooves 125 of the inner wall 129. The protuberances 136 allow the body portion 120 to be easily inserted and removed from the passageway 129 of the body portion 120 by simply pushing or pulling the body portion 120 from the passageway 129 thereby causing the protuberances 136 to disengage from the grooves 125. Alternatively, the receptacle portion 130 may comprise a unitary structure to receive and store tissue or debris during the biopsy procedure (FIG. 4). In this embodiment, the tissue or debris may be stored within the receptacle 130 until removal of the device 100 from the endoscope.

Referring to FIG. 6, the protuberances 136 may be oval and located along the surface of the receptacle portion 130. However, in an alternate embodiment, the protuberances 136 can include a variety of shapes and can be positioned in a variety of locations suitable for securely connecting the receptacle portion 130 with the body portion 120 of the biopsy collection device 100. In this embodiment, after withdrawal of the medical device from the passageway 129, the receptacle portion 120 can be removed and the tissue or debris is retrieved.

Figure 12:
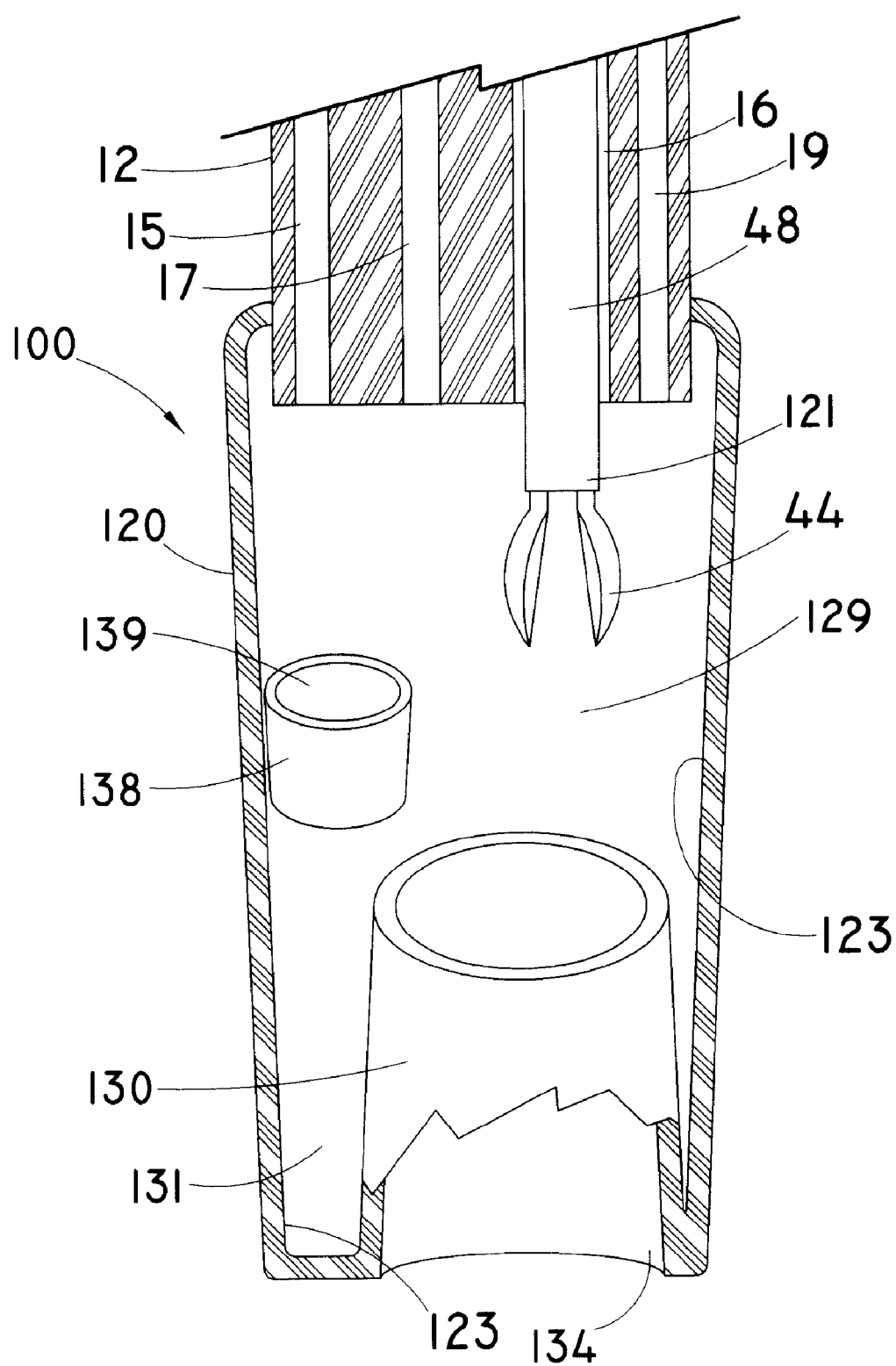
FIG. 12 is partial cross-sectional view of a one-piece biopsy collection device having a secondary receptacle portion, wherein the pair of forceps is inserted into the passageway of the body portion of the biopsy collection device.

In another embodiment of the present invention, the biopsy collection device 100 can also comprise one or more secondary receptacle portions 138 disposed within the passageway 129 of the biopsy collection device 100 (see FIG. 12). Secondary receptacles may also be formed in the distal end 134 by dividing the receptacle portion 130 into additional receptacles as described above. See for example, FIGS. 14-18. As shown in FIG. 12, the secondary receptacle portion 138 provides the lumen 139 to receive multiple samples of tissue or debris during the biopsy procedure. Samples of tissue and debris may be taken from a first biopsy site and collected in the lumen 131 of the receptacle portion 130 of the biopsy collection device 100. The secondary receptacle portion 138 further allows a second sample of tissue to be collected, for example, at a second biopsy site. Additional receptacle portions 138 may also be provided in the biopsy collection device 100 when multiple biopsy samples are to be collected from multiple biopsy sites, i.e. one receptacle portion may be provided for each biopsy site. Similarly, the lumen 131 may be subdivided using wall partitions 152. The receptacles 130, 138 and lumens 131, 139, therein may be marked to be visible to the operator of the biopsy device to be able to distinguish the different biopsy sample locations. For example, a first lumen 131 may be marked with a unique indicia that is viewable by the operator and subsequent lumens may be marked with differing unique indicia. Similarly, a first lumen 131 may be marked with a unique indicia and the operator may place samples in a clockwise or counterclockwise direction around the receptacle 130 so that the operator would know which sample was taken first, second, etc. Additionally, there is no need to repeatedly withdraw the biopsy forceps or other medical devices during the collection of multiple tissue or debris samples. Thus, multiple samples from various target sites can be easily stored and retrieved. After completion of the biopsy procedure, the biopsy collection device 100 is disengaged from the attached endoscope 10 and the multiple samples of tissue or debris are collected.

Figure 3:
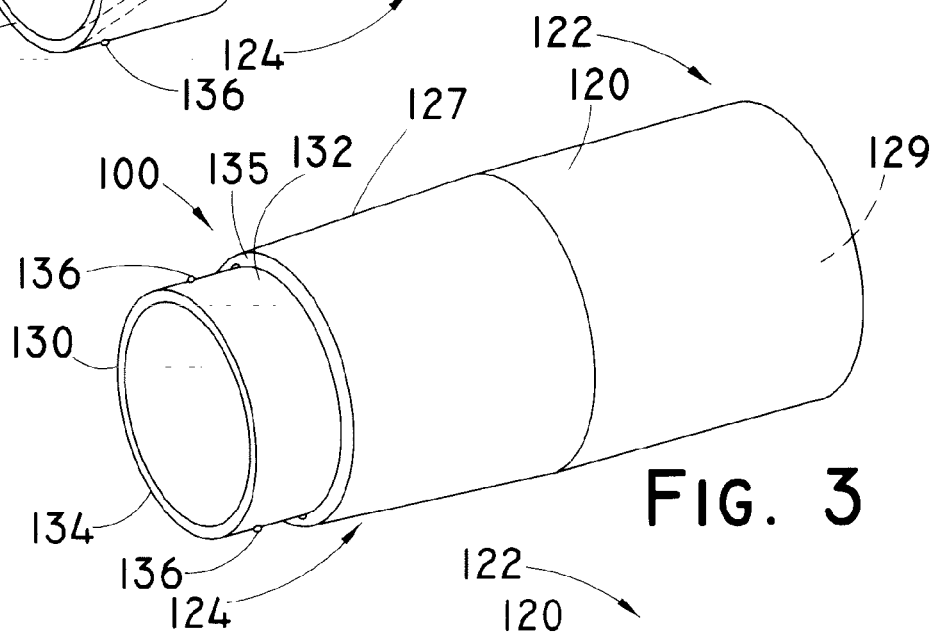
FIG. 3 is a perspective view of the body portion and the receptacle portion of the biopsy collection device of FIG. 2 in a partially connected configuration.

Referring to FIGS. 2-4, the biopsy collection device 100 may include a tapered distal end 124 provided with an atraumatic tip which includes both a conical taper 127 and a bevel 135 the distal end. The atraumatic tip of the biopsy collection device 100 reduces the potential damage to the patient during delivery of the device 100. As such, the bevel edges of the biopsy collection device 100 present few, if any, sharp edges. The conical taper 127 also allows the biopsy collection device 100 to be easily maneuvered as it is engaged and disengaged from the endoscope 10 utilizing a snap-fit connection.

In an alternate embodiment, the body portion 120 can also comprise a side outlet port (not shown) located along the outer surface of the biopsy collection device 100. The outlet port provides an exit for any medical devices to pass through the passageway of the biopsy collection device during a biopsy procedure.

Figure 8:
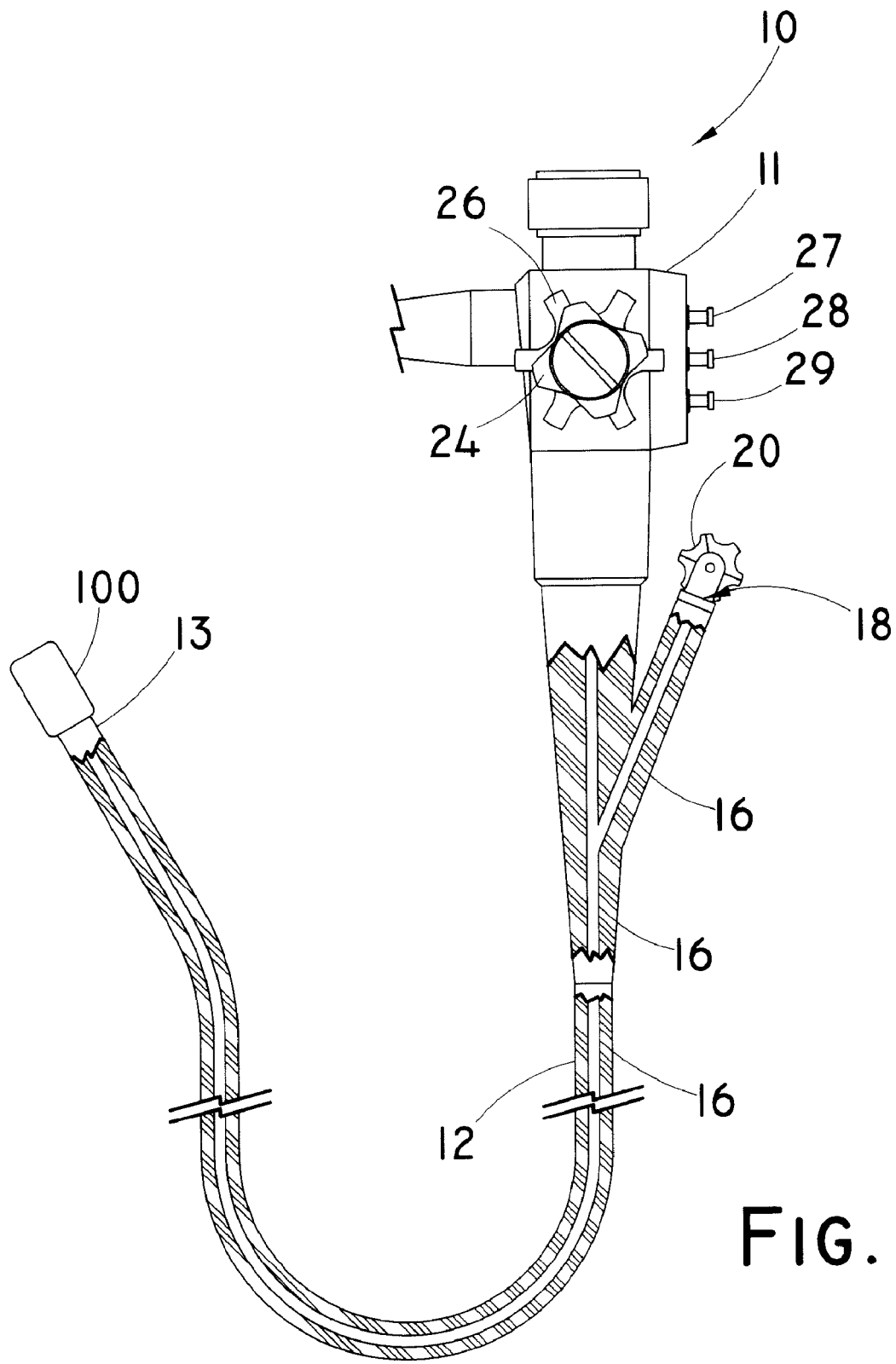
FIG. 8 is a partial cross-sectional view of the biopsy collection device attached to the endoscope of FIG. 1.
Figure 10:
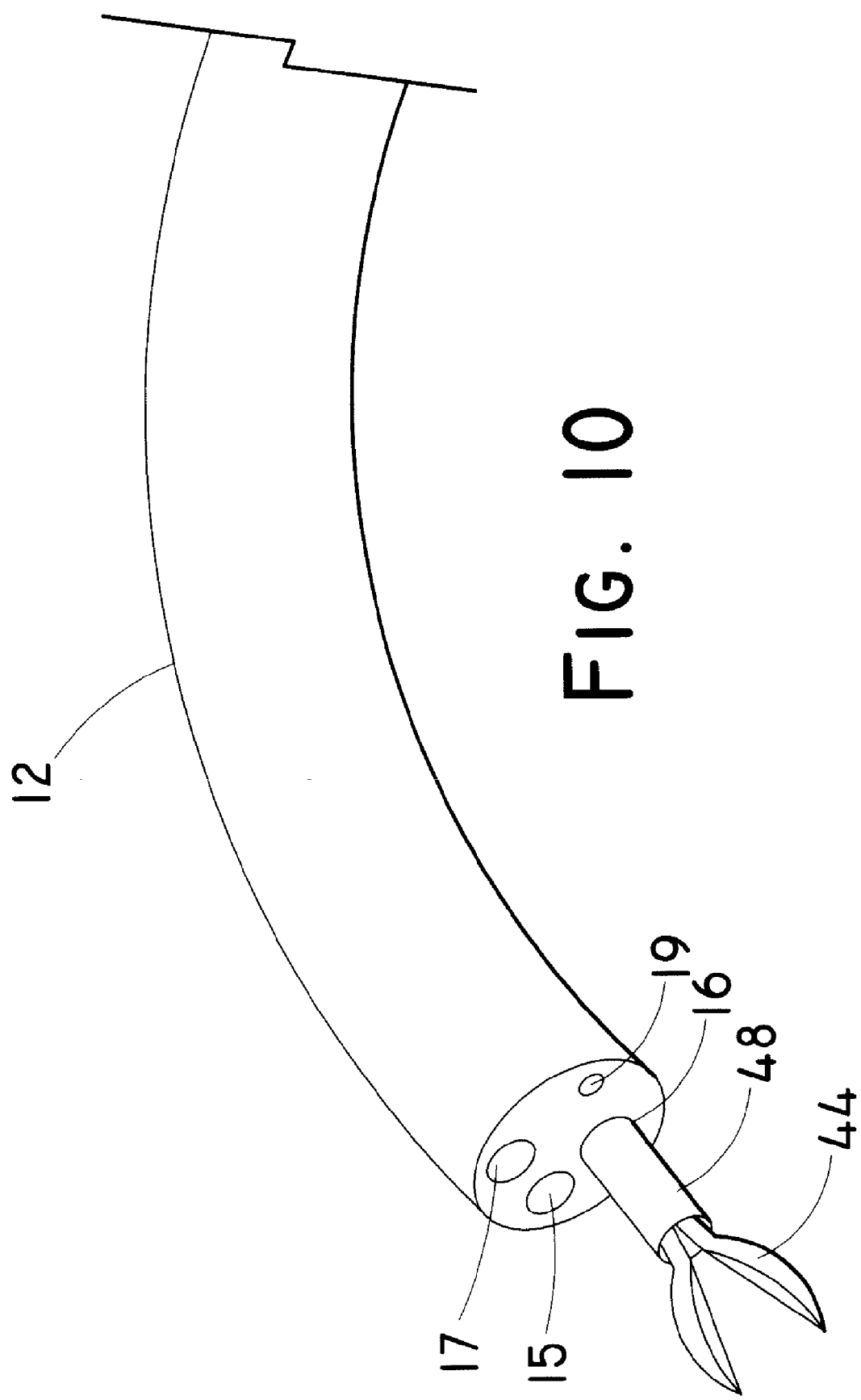
FIG. 10 is a cross-sectional view of a portion of the endoscope of FIG. 9.

FIG. 8 is a partial cross-sectional view of the endoscope 10 and attached biopsy collection device 100. The endoscope 10 includes the operating biopsy channel 16 which extends from the biopsy port 18 to the insertion tube 12. The insertion tube 12 leads to the attached biopsy collection device 100. As shown in FIG. 10, the insertion tube 12 includes a plurality of channels through which medical devices, such as forceps or a cutting device, may be disposed. In addition to the biopsy channel 16, the insertion tube provides a suction channel 15, an air/water channel 17 and a viewing channel 19. The present invention is not limited to the above mentioned channels and other embodiments may include varying combination of channels to accommodate other medical devices.

Figure 9:
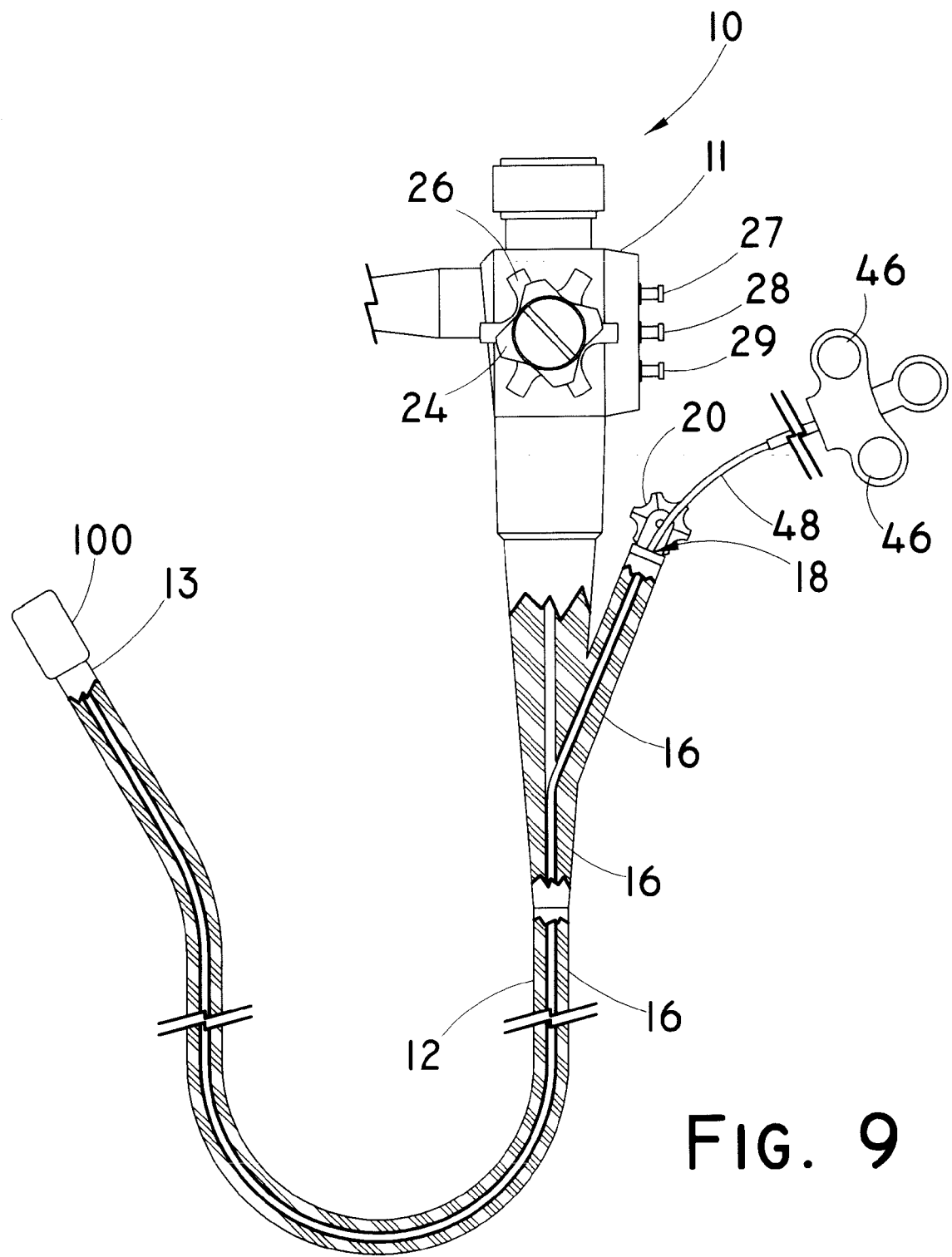
FIG. 9 is a partial cross-sectional view of the biopsy collection device attached to the endoscope of FIG. 1 wherein a pair of forceps is inserted within the biopsy channel of the endoscope to remove tissue from target site.

As shown in FIGS. 8 and 9, the operating control portion 11 of the endoscope 10 is in mechanical and fluid communication with the insertion tube 12. The control portion 11 is configured to control the insertion tube 12 and endoscopic parts disposed therein. As shown, the control portion 11 includes first and second control knobs 24, 26. The control knobs 24, 26 are configured to be in mechanical communication with the insertion tube 12. The control knobs 24, 26 allow the physician to control and guide, by known means, the insertion tube 12 through the vessels and cavities of the patient. The control portion 11 may further include a plurality of ports, such as a suction port 27, an air/water port 28 and a camera port 29. Each of the ports of the endoscope 10 is in communication to one of the channels of the insertion tube 12. For example, the suction port 27, when activated, allows a vacuum from a suction source through the suction channel 15 for suctioning unwanted plaque and debris from the patient. Likewise, the air/water port 28, when activated, allows air and water through the air/water channel 17 for flushing removing tissue and/or debris from the patient. Also, the camera port 29, when activated, allows a visual image of the target site through the viewing channel 19 for positioning and removing of tissue and/or debris from the patient. Additionally, the endoscope 10 includes a biopsy control knob 20 to control and guide the medical device inserted through the biopsy channel 16.

Referring to FIG. 9, the exemplary pair of forceps 44 is extended along the operating biopsy channel 16 to the target site after a portion of tissue has been incised with a cutting device (not shown). The forceps 44 are inserted and extended into the biopsy channel 16 through a lumen of a catheter 48 to the target site for grasping the incised tissue and delivering the tissue to the biopsy collection device 100 for removal. The catheter 48 is a flexible tubular member formed from any semi-rigid polymer. For example, the catheter 48 can be formed from polyurethane, polyethylene, tetrafluoroethylene, polytetrafluoroethylene, perfluoalkoxl, fluorinated ethylene propylene, or the like. In a typical application, the catheter 48 may have a length of about 220 centimeters in order to sufficiently extend through the operating biopsy channel 16 of the endoscope 10. Catheter 48 may also have an outer diameter from about 6 to 7 French in order to fit within the operating biopsy channel 16. The catheter 48 may also have a hydrophilic coating overlying its outer surface. The hydrophilic coating, when applied to the outer surface of the catheter 48, imparts suppleness and kink resistance to the catheter 48. Hydrophilic coating also provides a highly lubricated surface to facilitate movement through the operating biopsy channel 16 of the endoscope 10.

Still referring to FIG. 9, the forceps 44 can include a pair of opposed finger rings 46 which enable a user to grasp the same and advance the forceps 44 towards the distal end 13 of the endoscope 10 to remove tissue from the target site.

FIG. 11 illustrates the biopsy collection device 100 of FIG. 8, wherein a medical device, such as a pair of forceps 44, is inserted through the biopsy channel 16 of the endoscope 10. The forceps 44 are utilized during the biopsy procedure to remove tissue after the tissue as been cut from a target site within a body cavity. The forceps 44 can be slidably disposed through the biopsy channel 16 into the body passage 129 of the biopsy collection device 100.

As illustrated in FIGS. 10-11, the forceps 44 may be incrementally moved along the operating biopsy channel 16 to enable controlled extension of the forceps 44 into the passageway 129 of the biopsy collection device 100 located at the distal end 13 of the endoscope 10. The forceps 44 also facilitate the controlled positioning of tissue during the removal of tissue from the target site and delivery to the biopsy collection device 100. Although FIG. 9 shows forceps 44 as the apparatus for removing tissue from the target site, other devices will become apparent to one of ordinary skill in the art and are intended to be within the scope of the embodiment.

In an alternate embodiment, a hypodermic needle can also be movably disposed within a channel of the endoscope 10 to assist in the removal of the tissue at the target site. For example, referring to FIG. 18, a needle 152 may be inserted into a port of the endoscope 10 and delivered to the tissue, for example through the catheter 48. The needle 152 may be used to inject any type of physiological saline solution that is known in the art into tissue. This causes the tissue at the target site to elevate from the underlying normal tissue. Elevation of the tissue at the target site facilitates removal of the cancerous tissue or other types of abnormal tissue during a biopsy procedure. The ability to remove the abnormal tissue without cutting into it enables a more accurate assessment of the tissue than would otherwise be possible if sampling a fragmented tissue sample. Furthermore, fragmented resection of early cancers may lead to a higher rate of local tumor recurrence. The needle 152 may also be used for obtaining tissue sample directly. Although FIG. 9 illustrates forceps 44 and catheter 48 disposed within the biopsy channel 16 of the endoscope 10, the endoscope 10 may contain multiple ports and/or channels adapted for separately receiving other devices, such as needles or other suitable devices, utilized during the biopsy procedure. The multiple channels can be used in connection with the secondary receptacle portion 136 to secure multiple samples of tissue or debris within the biopsy collection device 100 (see FIG. 12) during the biopsy procedure.

A method of using the biopsy collection device 100 will now be described with reference to FIGS. 8-13. In particular, and by way of example, FIGS. 8-13 illustrate a method for performing a biopsy procedure utilizing the biopsy collection device 100 to remove tissue from the target site. The method includes the step of attaching the biopsy collection device 100 to the endoscope 10 and delivering the device 100 to the target site of the patient.

The method also includes a cutting device (not shown) inserted through the operating biopsy channel 16 of the endoscope 10 to incise tissue from the target site prior to removal. For example, a typical needle knife or other suitable device may be loaded into an accessory channel of the endoscope 10 to facilitate the cutting of the tissue from the target site. Such methods for incising tissue at the target site are well known to those of ordinary skill in the art. Alternatively, in other embodiments a cutting device may be omitted from the method as tissue from the target site may not be intended to be cut, as is the case of removing debris or other material from the target site.

Figure 13:
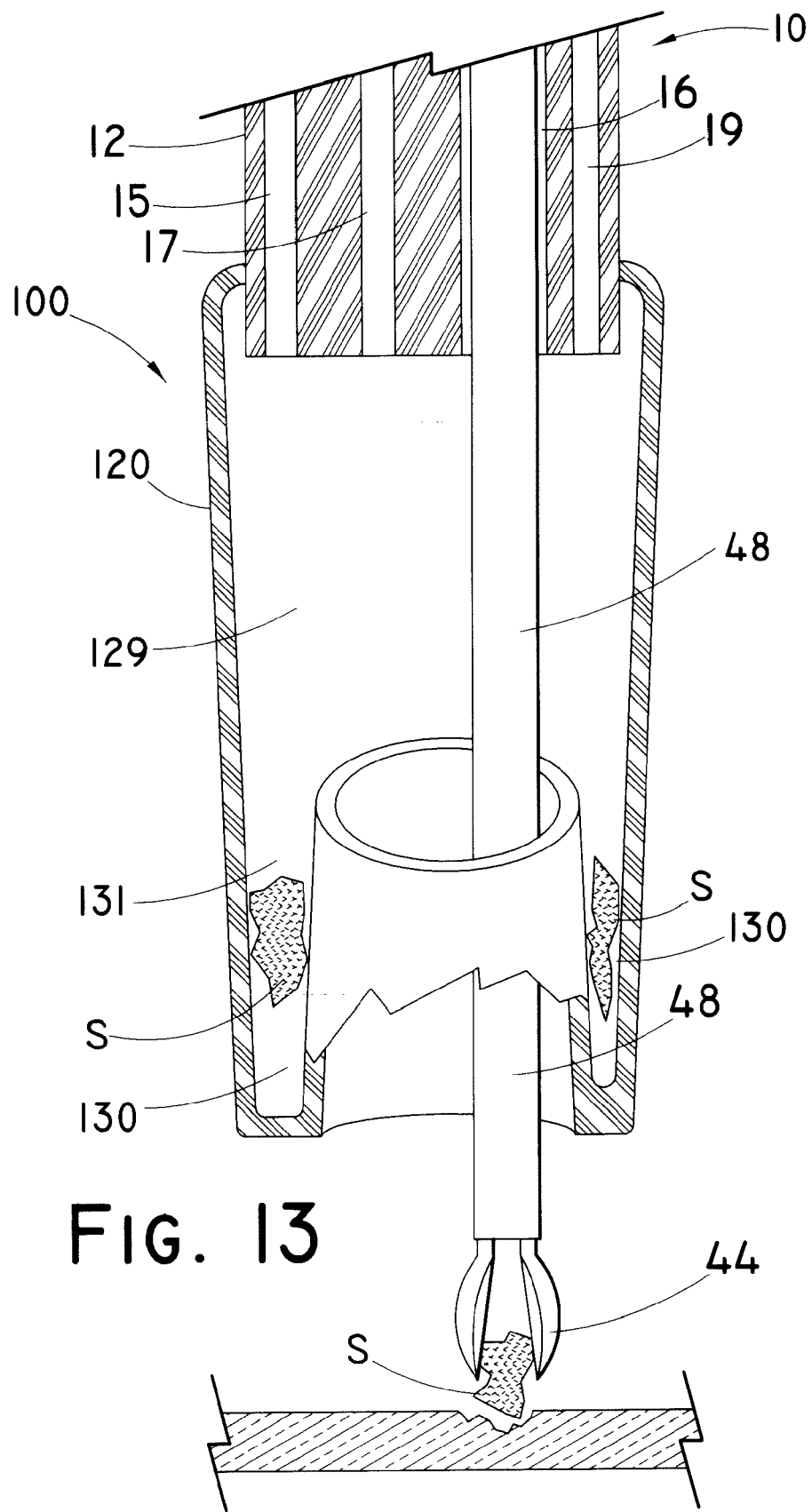
FIG. 13 is a partial cross-sectional view of a one-piece biopsy collection device showing the pair of forceps obtaining a biopsy sample.

Referring to FIG. 9, the method also includes the step of advancing forceps 44 through the operating biopsy channel 16 of the endoscope 10. The forceps 44 are maneuvered through the channel 16 into a patient down through the esophagus and duodenum, towards the target site within the gastrointestinal lumen. During advancement of the forceps 44 to the target site, the distal end of the forceps 44 is extended within the lumen of the catheter 48 to grasp the incised tissue for delivery to the biopsy collection device 100, as shown in FIG. 13.

FIG. 11 is a partial cross-sectional view of the biopsy collection device 100 in close proximity to the tissue at the target site to be removed from the target site. After selectively positioning the biopsy collection device 100 in proximity to the target site, the method can further include the step of removing tissue or debris from the target site as shown in FIG. 13 using the medical device to retain the tissue sample. The medical device is retracted into the biopsy collection device 100 and the tissue or debris may be placed into the receptacle portion 130 of the biopsy collection device 100. Upon removal of the device 100 from the attached endoscope 10, the tissue or debris is completely removed from the device. Alternatively, a flushing liquid, such as a saline solution, can be introduced to flush and remove the tissue or debris from the from the biopsy collection device 100.

Figure 18:
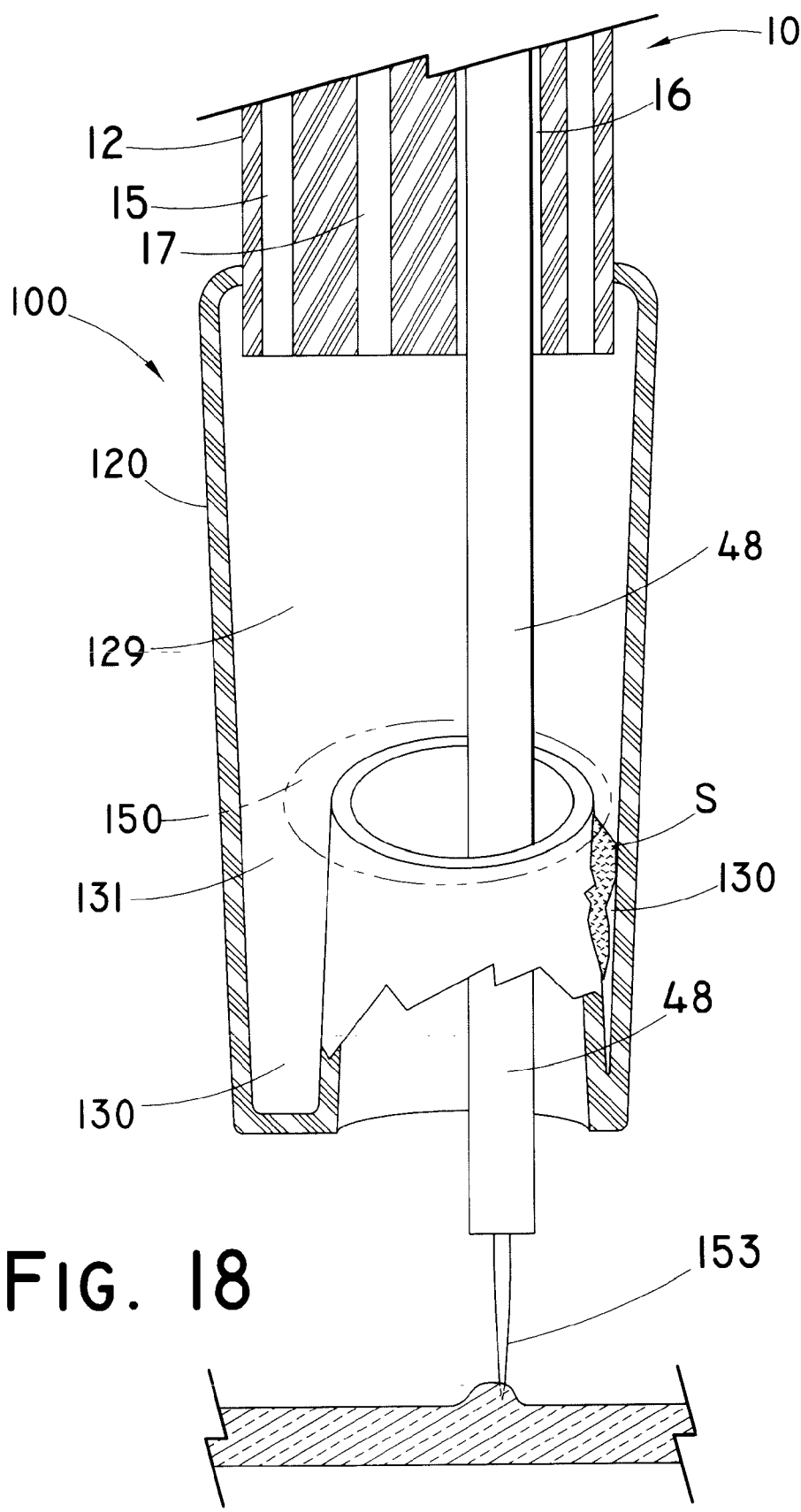
FIG. 18 is a partial cross-sectional view of a biopsy collection device showing a needle device.

In another embodiment of the present invention, the method of removing tissue with the biopsy collection device 100 may also include the step of formatting a protrusion of the target site, after selectively positioning the biopsy collection device 100 in close proximity to the target site. The protrusion is created by injecting physiological saline solution through a needle 152, which may be disposed within the lumen of the catheter 48 as shown in FIG. 18. The needle 152 may be inserted through the port 18, shown in FIG. 9. The needle 152 may be disposed in the same lumen as the forceps 44 and extended beyond the distal end of the catheter 48 until it contacts target site. The physiological saline solution lifts the target site from the surrounding submucosa tissue, thus enabling subsequent incision of the elevated target site without inadvertently injuring the surrounding submucosa tissue. A sufficient amount of saline solution, as is known in the art, is injected to elevate the target site and separate it from the underlying submucosa tissue. After injection of the physiological saline is completed, the needle 152 is retracted within the lumen. The needle may also be used for obtaining a biopsy and is not limited to a particular channel and may be inserted through other channels of the endoscope 10.

After the tissue at the target site has been sufficiently elevated, the process of creating the incision allows the tissue to be cut and removed. In particular, the distal end of the catheter 48 is advanced into the target site with the forceps 44 remaining retracted within the lumen of the catheter 48 until delivery to the target site to remove the incised tissue and insert the tissue into the biopsy collection device 100.

After the distal end of the catheter 48 is contained within the target site, the forceps 44 may be advanced distally past the distal end of the catheter 48 and into the tissue of target site. As the forceps 44 extend distally and into the target site, the tissue is grasped and removed from the biopsy site. The forceps 44 are retracted into the biopsy collection device 100 and the tissue sample is securely delivered to the lumen 131 of the receptacle 130 of the biopsy collection device 100. As described above, multiple tissue samples may be biopsied and stored in the receptacles 130, 138 of the biopsy collection device 100 by repeating the sampling method and delivering the sample to the appropriate receptacle.

After the tissue from the target site has been delivered to the biopsy collection device 100, the handle assembly 46 may be pulled to withdraw the forceps 44 through the endoscope 10. Subsequently, the endoscope 10 and attached biopsy collection device 100 can be removed and the tissue can be retrieved from the biopsy collection device 100.

The above figures and disclosure are intended to be illustrative and not exhaustive. This description will suggest many variations and alternatives to one of ordinary skill in the art. All such variations and alternatives are intended to be encompassed within the scope of the attached claims. Those familiar with the art may recognize other equivalents to the specific embodiments described herein which equivalents are also intended to be encompassed by the attached claims.

The invention claimed is:

1. A biopsy collection device comprising:
a body portion having a proximal end portion and a distal end portion, the proximal end portion configured for attachment to an endoscope;
a passageway extending through the body portion, the passageway configured to receive a biopsy sampling device extending from the endoscope and passing through the passageway to a target site; and
a receptacle portion at the distal end portion, the receptacle portion including a wall extending proximally from the distal end portion into an interior of the body portion, the wall at least partially defining an opening to the receptacle portion; the receptacle portion operably connected to the passageway and configured to retain a sample removed from the target site during a biopsy procedure.

2. The biopsy collection device of claim 1, wherein the opening is configured to inhibit the passage of the sample out of the receptacle portion and configured to allow passage of the biopsy sampling device therethrough.

3. The biopsy collection device of claim 1, wherein the wall is tapered to form a portion of the receptacle portion.

4. The biopsy collection device of claim 1, further comprising an endoscope wherein the proximal end portion is attached to the endoscope.

5. The biopsy collection device of claim 1, wherein at least a portion of the biopsy collection device is constructed to permit viewing therethrough of the target site.

6. The biopsy collection device of claim 1, wherein the body portion and the receptacle portion are formed by unitary construction.

7. The biopsy collection device of claim 1, wherein the receptacle portion is releasably connected to the body portion.

8. The biopsy collection device of claim 7, wherein one of the receptacle portion and the body portion comprises a protuberance and the other of the receptacle and the body portion comprises a groove sized and shaped to receive the protuberance and connect the receptacle to the body portion.

9. The biopsy collection device of claim 1, wherein the distal end portion of the body comprises an atraumatic tip.

10. The biopsy collection device of claim 1, wherein the device comprises a conical taper so that a distal end portion diameter is smaller than a proximal end portion diameter.

11. The biopsy collection device of claim 1, wherein the receptacle portion includes a plurality of walls extending proximally from the distal end portion into an interior of the body portion, one of the plurality of walls at least partially defining an opening to the receptacle portion.

12. A biopsy collection device comprising:
a body portion having a proximal end portion and a distal end portion and a body wall extending between the proximal end portion and the distal end portion, the proximal end portion configured for attachment to an endoscope, the distal end portion having an opening defined therethrough; and
a receptacle portion at the distal end portion, the receptacle portion including a receptacle wall extending proximally from the distal end portion into an interior of the body portion, the receptacle wall and the body wall at least partially defining a lumen configured to retain a sample removed from a target site during a biopsy procedure, the receptacle wall at least partially defining the opening through the distal end portion, the opening configured to receive a biopsy sampling device extending from the endoscope to the target site.

13. The biopsy collection device of claim 12, wherein the biopsy collection device comprises a viewing portion.

14. The biopsy collection device of claim 12, wherein the receptacle portion comprises a plurality of lumens for retaining samples therein.

15. The biopsy collection device of claim 14, wherein at least one of the plurality of lumens includes a unique indicia for allowing identification of the sample retained therein.

16. The biopsy collection device of claim 12, wherein the lumen is sized and shaped to inhibit the passage of the sample out of the receptacle portion.

17. A biopsy collection system comprising:
a biopsy collection device comprising:
a body portion having a proximal end portion and a distal end portion and a body wall extending between the proximal end portion and the distal end portion, the proximal end portion configured for attachment to an endoscope, the distal end portion having an opening defined therethrough; and
a receptacle portion at the distal end portion, the receptacle portion including a receptacle wall extending proximally from the distal end portion into an interior of the body portion, the receptacle wall and the body wall at least partially defining a lumen configured to retain a sample removed from a target site during a biopsy procedure, the receptacle wall at least partially defining the opening through the distal end portion; and
a biopsy sampling device, the biopsy sampling device sized and shaped so that a distal end of the sampling device is extendable through the opening defined in the distal end portion of the body and the biopsy sampling device is configured to remove and release the sample in the receptacle portion.

18. The biopsy collection system of claim 17, wherein the biopsy sampling device is a pair of forceps.

19. The biopsy collection system of claim 17, wherein the biopsy sampling device is a needle.

20. The biopsy collection system of claim 17, wherein the opening is centrally positioned.

* * * * *